United States Patent [19]

Dehazya

[11] Patent Number: 5,281,582
[45] Date of Patent: Jan. 25, 1994

[54] SERUM GROWTH FACTOR

[75] Inventor: Philip Dehazya, Cuddebackville, N.Y.

[73] Assignee: Alliance Pharmaceuticals, Corp., Otisville, N.Y.

[21] Appl. No.: 843,920

[22] Filed: Feb. 27, 1992

[51] Int. Cl.$^5$ .............................................. A61K 37/36
[52] U.S. Cl. ......................................... 514/21; 514/4; 530/363; 530/364; 530/362
[58] Field of Search ...................... 514/4, 21; 530/362, 530/363, 364

[56] References Cited

U.S. PATENT DOCUMENTS 4,963,529 10/1990 Fujioka et al. ........................ 514/12
5,093,317 3/1992 Lewis et al. ............................ 514/4

FOREIGN PATENT DOCUMENTS 9116335 10/1991 World Int. Prop. O. .
9118924 12/1991 World Int. Prop. O. .

OTHER PUBLICATIONS

Peach et al. Biochim. Biophys Acta 1097 1991 49–54.
The Plasma Proteins: Structure, Function, & Genetic Control: 63–70 & 134–141 (1975).
Day, et al. J. Biological Chem. 264: 595–597 (1979).
Dolhofer, et al., FEBS Letters 103: 282–286 (1979).
Williams, et al. PNAS (USA) 78: 2393–2397 (1981).
Shaklai, et al. J. Biological Chem. 259: 3812–3817 (1984).
Rendell, et al. J. Laboratory & Clinical Med. 105: 63–69 (1985).
Iberg, et al. J. Biological Chem. 261: 13542–13545 (1986).
Morris, et al. Biochem. Med. & Metabolic Biology 35: 267–270 (1986).
Simpietro, et al. The Lancet: 994–996 (1987).
Shima, et al. Diabetologia 35: 627–631 (1988).
Ammanannati, et al. Arzneim.-Forsch/Drug Res. 39: 661–664 (1989).
Aring, et al. Biochimica et Biophysica Atca 1010: 140–144 (1989).
Cohen, et al. J. Immunological Methods 117: 121–129 (1989).
Gabius, et al. Histochemistry 91: 5–11 (1989).
Murphy. Int'l J. Cell Cloning 8: 138–145 (1990).
Smith, et al. Pharmaceutical Res. 6: 466–473 (1989).
Svacina, et al. Computer Methods and Programs in Biomedicine 32: 259–263 (1990).
Ahmed, et al. Analyitcal Biochemistry 192: 109–111 (1991).
Peach, et al. Biochimica et Biophysica Acta 1097: 49–54 (1991).
Zaitsu, et al. J. of Cell. Physiology 149: 339–346 (1991).

*Primary Examiner*—Howard E. Schain
*Assistant Examiner*—P. Lynn Touzeau
*Attorney, Agent, or Firm*—Knobbe, Martens, Olson & Bear

[57] ABSTRACT

A novel glycosylated form of albumin designated EGA and isolated from biological fluids is further characterized by its cell growth promoting activity. A process of isolation of human or bovine glycosylated albumin is described. The EGA fractions have been identified by serological histochemical and biological assays as well as lectin reactivity. The growth-promoting effect of EGA is directed to various transformed cell lines and primary cells of mammalian origin. Hepatoma cells have been found to produce EGA, in vitro. Novel compositions of EGA containing media are provided for cell, tissue or organ culture.

23 Claims, 8 Drawing Sheets

FIG. 9

SERUM GROWTH FACTOR

FIELD OF INVENTION

The present invention relates to an oligo-glycosylated form of albumin present in blood and other bodily fluids. There are described herein compositions and methods for the preparation and the use of the glycosylated albumin for cell growth, cell proliferation, enhancement of cell growth, cell differentiation and maturation, diagnosis and clinical applications.

BACKGROUND OF THE INVENTION

In general, albumins are widely found in living material and known as simple proteins defined as yielding only alpha-amino acids and their derivatives on complete hydrolysis. They are mainly characterized by solubility in water and dilute aqueous salt solutions.

As simple proteins, albumins are not conjugated. Conjugated proteins are defined as containing a protein molecule bound to an organic, nonprotein prosthetic group.

Among those albumins isolated into crystalline form, serum albumin has been determined to possess a molecular weight of 65,000 to 69,000 daltons. The pI values range from 4.7 to 4.9. The molecular weight of bovine albumin on the basis of its amino acid sequence has been estimated at about 67,300 daltons. (See also The Plasma Proteins, F. W. Putnam, ed., Vol. 1, 1975, Academic Press).

Serum albumin is the principal serum protein of mammalian organism. In humans, the normal blood plasma range is 3.5–5.0 g of albumin/100 ml (or per dl). Albumin is also found in the extravascular spaces, the lymph, and in other biological fluids including e.g. amniotic fluid, bile, gastric juice, sweat and tears. Albumin is a major component of edema fluid. In fact, plasma albumin has been determined to have two major functions, one is maintenance of osmotic pressure, the other is transport of noncovalently bound substances. Such substances comprise metals and other ions, bilirubin, amino acids, fatty acids, enzymes, hormones and drugs. More recently, albumin has also been characterized in diabetic condition as capable of nonenzymatically binding several glucose molecules.

Albumin is produced substantially in the liver. In fact, liver cells or hepatocytes principally produce albumin. In a 70 kg human, the liver synthesizes about 12–14 g albumin per day. Albumin has a half life of about 20 days in man. Albumin synthesis comprises the classical intracellular assembly of 575 amino acids. Its secretion is inhibited by ouabain. Albumin synthesis is stimulated in vivo by cortisone and thyroid hormones (thyroxine and triiodothyronine). Albumin synthesis in vitro appears dependent on osmotic pressure such that it is increased under hypotonic and decreased under hypertonic conditions.

Due to its small size, albumin leaks through blood vessel walls into extravascular space to be returned to the blood circulatory system by the lymphatic system. In patients with kidney disease, albumin is known to pass into urine, frequently leading to hypoalbuminia.

It has been commonly accepted that serum albumin (or plasma albumin) is alone among major plasma proteins in that it contains no carbohydrate (Eylar, J. Theor. Biol. 19, 89, 1965).

However, nonenzymatic glycosylation or glycation of albumin in patients suffering from diabetes mellitus has been observed as the consequence of the condensation reaction between relatively high concentrations of glucose and the free amino group at the N-terminus or epsilon-amino group of lysine residues exposed on the albumin molecule. The reaction proceeds by Schiff base formation between carbonyl groups of glucose and the free amino groups. However, the nonenzymatic formation of a ketoamino is slow and concentration dependent. Thus prolonged hyperglycemia may increase the glycation level of albumin, in addition to that of many other serum proteins Moreover, the hitherto described glycated albumins appeared to contain only one sugar residue per binding site.

More recently, Robert J. Peach et al. (Biochimica et Biophysica Acta 1097 (1991) 49–54) characterized a new mutant form of albumin (Albumin Casebrook) carrying a single N-linked oligosaccharide which binds to Concanavalin A. The albumin variant constitutes about 35% of total serum albumin.

Surprisingly, a minor glycosylated albumin fraction has now been discovered as generally present in mammalian blood. The isolated protein exhibits a growth promoting and modulating effect in serum-free cultures of various cell types. While the biological role of this new circulating factor is still unknown, it has potential utility in the diagnosis and treatment of the processes of cell or tissue growth, development, differentiation and healing.

SUMMARY OF THE INVENTION

According to the present invention, there is provided a glycosylated albumin (glycoalbumin EGA) which can be purified from plasma or serum.

The growth factor in the form of glycosylated albumin according to the present invention provides a growth promoting or potentiating effect on serum-free cell cultures.

Further to the present invention, the instant glycoalbumin derived from biological fluids is characterized as a mainly a single band moving on SDS/PAGE with an apparent molecular weight of at least 65,000 daltons. The isolated glycoprotein can be identified by serological means as an albumin, by specific glycosidase action or lectin reactivity as carrying oligosaccharides and consequently enzymatically glycosylated, and by addition to serum-free cell cultures as having growth stimulating, modulating or sustaining effect on various cell types.

Further to the identification of the purified fraction, the glycosylated albumin, EGA, was analyzed through sequencing and computer assisted sequence matching. The N-terminal sequence of bovine EGA was found to be that of bovine albumin, namely, asp, thr, his, lys, ser, glu, ile, ala, his, arg (Brown, 1975, Fed. Proc. 34:591).

The present invention further provides a glycosylated albumin which binds to the surface of various cell types. In this context, the cell receptors for the inventive glycosylated albumin appears to be cell state-specific. The portion of the cell cycle exhibiting the most binding of albumin include the $G_0/G_1$ and early S phases.

The present invention is directed to a cell surface binding and growth activity which can be abolished by proteolysis or deglycosylation.

The glycosylated albumin fraction having CHO cell growth promoting activity according to the present invention is further characterized by isoelectric focusing (IEF) showing about four major bands and several minor ones a pI of about 3.5–4.1.

The present invention is directed to an oligoglycosylated bovine albumin characterized by an N-terminal amino acid sequence (ca. 10 amino acids) which is identical with the known bovine albumin sequence.

The instant presumably enzymatically glycosylated albumin growth factor is characterized by the presence of at least one oligosaccharide chain, wherein the putative terminal sugar residue can be removed by neuraminidase followed by sequential removal of sugar residues with specific glycosidases. Both N- and O- linked oligosaccharide forms have been observed.

Removal of N-linked oligosaccharide from the instant glycosylated albumin abolishes the growth promoting activity.

The present invention is also directed to a process of purifying oligo-glycosylated albumin (also designated as glycoalbumin or enzymatically glycosylated albumin, EGA) from blood or other body fluids comprising the steps of removing cells, debris or coagulated material from said fluids, before further purifying the growth factor by anion exchange chromatography, gel filtration, and pooling bioassay positive fractions and further purifying them by other means.

Another embodiment of the present invention is further directed to a process of purifying enzymatically glycosylated albumin (glycoalbumin) from blood comprising the steps of removing from blood plasma or serum proteins precipitated proteins in aqueous 50% saturated ammonium sulfate by centrifugation; dialyzing the supernatant containing unprecipitated matter against sodium acetate buffer, fractionating supernatant components by anion exchange chromatography using 3M NaCl salt step gradient elution in tris buffer at pH8.0; further fractionating the 3M NaCl eluate by size exclusion chromatography; collecting cell growth activating fractions in this buffer (pH8.6); and again fractionating the active factor by linear gradient cation exchange chromatography while determining the activity by a bioassay.

The present invention further provides a growth factor comprising glycoalbumin as produced by a hepatoma cell culture. In this context, the identification of the hepatoma-derived growth factor can be utilized in the growth regulation of the hepatoma cell culture. Moreover, the identification of the instant hepatoma-derived EGA growth factor can be applied to the diagnosis and treatment of hepatoma.

The present invention is also directed to the treatment of wounds using the glycoalbumin growth factor effect.

Another preferred embodiment of the present invention provides for a diagnostic test for liver pathology since liver is the main source for albumin and probably also EGA. The use of a combination of biochemical and immunochemical means as well as bioassay serves the diagnostic assessment of liver function.

The present invention is directed to a tissue and cell culture medium comprising a glycosylated albumin growth factor.

Moreover, in view of the growth-promoting activity of EGA, the present invention provides advantageous use of the EGA fractions as replacement of serum in compositions for cell, tissue or organ culture Further in this context, the growth promoting effect of EGA is advantageously effective on precursor or differentiated primary cells or tissue.

BRIEF DESCRIPTION OF THE FIGURES

FIG. 7 Human umbilical cord endothelial cells in Matrigel medium, supplemented with EGA, display capillary-like processes; micrographs with (A) 200× and (B) 400× optical enlargement;

DETAILED DESCRIPTION OF THE INVENTION

The novel glycosylated albumin has been identified in mammalian blood or other biological fluids. The instant glycoprotein or EGA is reactive with certain lectins which are specific for sialic acid or glucose based sugar residues. Its glycosylation is further demonstrated by chemical staining procedures. The chromatographically purified EGA fractions exhibit a broad growth promoting activity in cultures of various cell lines, which activity has been found sensitive to proteases and glycosidases.

Figure 1:
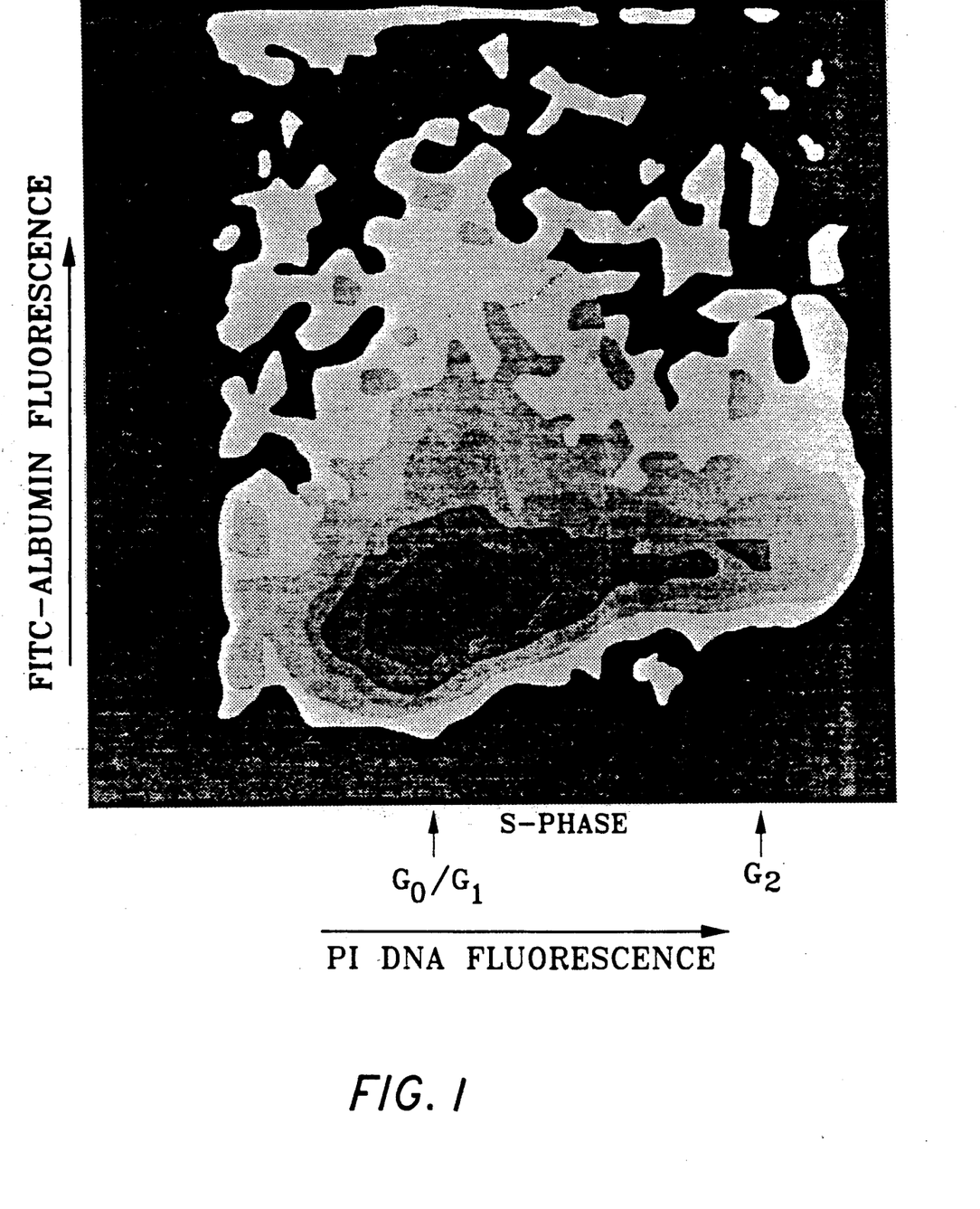
FIG. 1 Two-parameter analysis of FITC-EGA binding to CHO-KI cell surface showing the majority of binding during the $G_0/G_1/S$ phases of cell cycle; a total of 19371 cells were examined.

The instant glycoalbumin, EGA, crossreacts with anti-albumin antisera. EGA binds to various cells or more specifically, cell surface receptors. The presence of these receptors in cells appears to be cell cycle dependent. In particular, fluorochrome labelled EGA binding has been observed on cells at the $G_0$, $G_1$ or early S phase of the cell cycle, suggesting a cell cycle dependent expression of receptors or receptor conformation (FIG. 1).

In this context, the present invention provides a bioassay for determining the activity of the instant EGA fraction whereby the growth promoting effect of EGA is observed in serum free CHO cultures. It is known that CHO (Chinese hamster ovary) cells will not settle, adhere or grow on a solid matrix or tissue culture flasks in serum-free media. However, when serum-free media are supplemented with effective amounts of the instant glycosylated albumin, e.g. the human or bovine type (h-EGA or b-EGA), CHO cells will grow.

A further embodiment of the present invention provides an albumin from human or bovine biological fluids, preferably plasma or serum, which comprises glycosylated chains containing sialic acid or N-acetyl glucosamine residues, as well as galactosamine and galactosamine trimers (branched structures) and perhaps mannose.

The glycosylated albumin growth factor has been isolated from mammalian blood. It can also be derived from the conditioned media of hepatoma cells indicating that the growth factor like non-glycosylated albumin originates in vivo from the liver. EGA can be purified from its various sources including human or bovine blood serum or plasma.

Purification of Glycoalbumin

One preferred method for purifying the growth-promoting fraction of oligo-glycosylated albumin from bovine blood involves the following protocol.

A. Salt Precipitation

Citrated blood is centrifuged to remove blood cells and platelets. The cell-free supernatant plasma is mixed with an equal volume of saturated ammonium sulfate or adjusted to 50% in order to remove a large portion of the saturation with ammonium sulfate salt. The precipitated protein is centrifuged to a pellet. The supernatant liquid is decanted and dialyzed in 0.02M sodium acetate at pH5.9.

B. Column Chromatography

Figure 2:
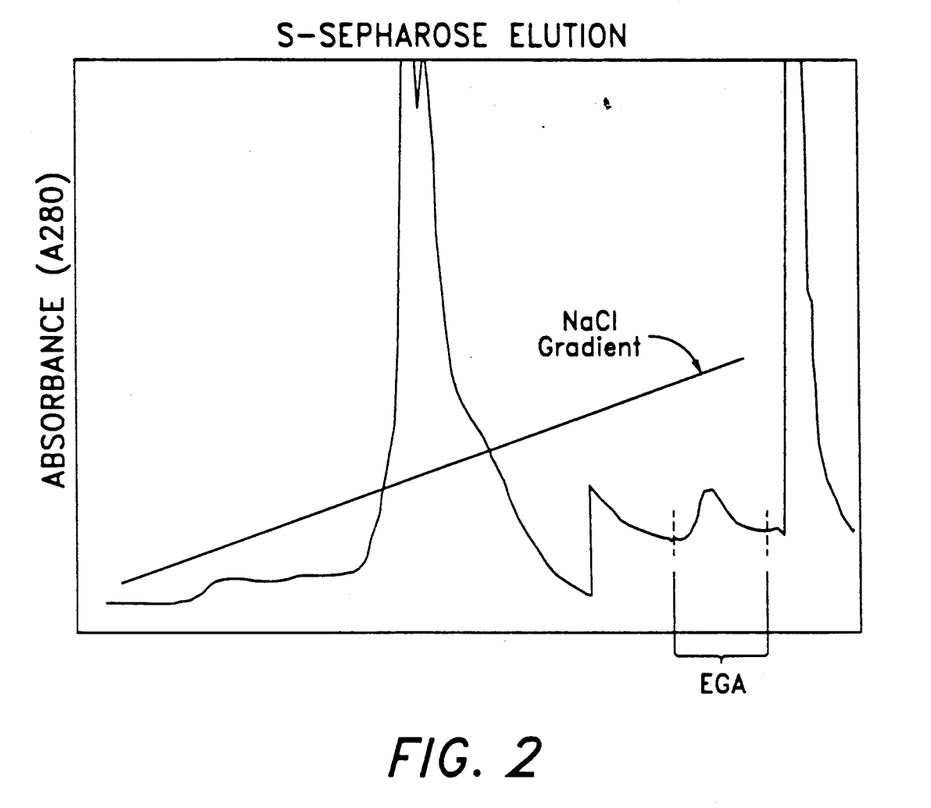
FIG. 2 S-Sepharose chromatography elution profile of the 50% sat. ammonium sulfate supernatant human plasma solution developed with a linear gradient of 0 to 0.2M NaCl in 20 mM sodium acetate buffer, pH 5.9., at 5° C. as described below. The biologically active peak is indicated as EGA.

The dialyzed supernatant fraction is loaded on a S-Sepharose (Pharmacia) anion exchange column (5×12 cm or 1.5×10 cm) and washed with 0.02M sodium acetate pH5.9. The active fraction is finally eluted with a linear gradient buffer of 0 to 0.2M NaCl at 5° C. (FIG. 2). After dialysis, this fraction is loaded on a Q-Sepharose column, washed and developed with 0.02M tris buffer containing 1.0M NaCl. The active Q-fractions are pooled and further purified by gel filtration chromatography with Sephacryl S-300 Hr (Pharmacia), column bed size is approximately 1.5×70 cm at a flow of 1.5 to 2 ml/min at 5° C. in 20 mM Tris-HCl 150 mM NaCl, pH7.5.

Another purification step is afforded by the use of boronate affinity chromatography, whereby fractions in 50 mM Gly/NaOH (pH9) buffer are developed from column of P60 resin by step gradient with increased amounts of sorbitol in the glycine buffer.

The active EGA fractions are selected on the basis of the CHO-bioassay described below (Examples 10–13).

C. Gel Electrophoresis

The purified protein can be identified by non-denaturing, non-reduced polyacrylamide gel electrophoresis using the Laemmli's method but without first boiling the sample in SDS and/or mercaptoethanol. Further, the band corresponding to bovine albumin or glycosylated albumin fractions is further identified in typical SDS-PAGE gels which are 10% polyacrylamide in the separation gel portion (U.K. Laemmli, 1970, Nature, vol. 227, pp. 680–685). Moreover, western blots of such slab gel have been prepared to probe the identity of EGA. (See Example 4 and FIGS. 4–6).

The various ways for chromatographic purification of the glycoalbumin of the present invention are illustrated at the hand of the following Examples.

EXAMPLE 1

Purification of Glycosylated Albumin

Figure 3:
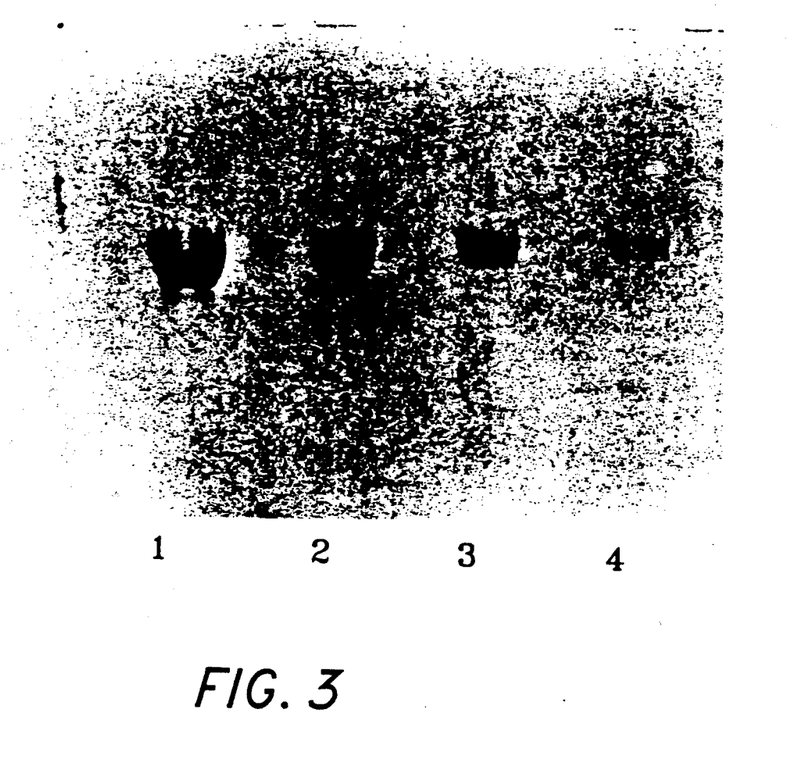
FIG. 3 An SDS-PAGE gel of purified EGA fractions containing 3, 1.5, 0.75, 0.375 µg protein per lane, respectively; Coomassie blue (C.B.) stain shows a single band.
Figure 6:
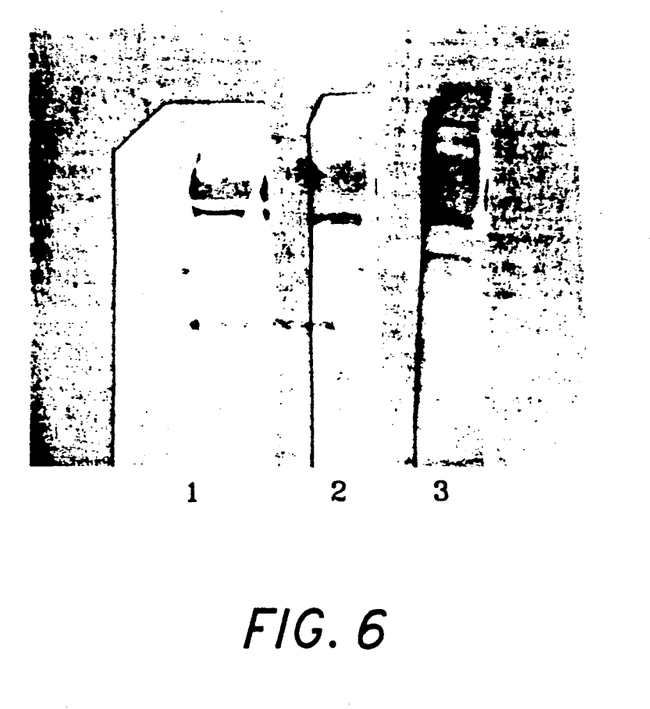
FIG. 6 Western blot analysis of glycosylated albumin which was purified from citrated human plasma fractionated by ammonium sulfate precipitation, S-Sepharose and gel filtration steps. Biologically active gel filtrate fractions were pooled, separated by non-reducing SDS-PAGE (-Mercaptoethanol) and transferred by the Western blot technique;
  Lane 1: Anti-albumin antibody detection;
  Lane 2: Application of biotinylated wheat germ lectin followed by alkaline phosphatase reaction for detection;
  Lane 3: Biotinylated S. nigra lectin and detection, as before.

Citrate-buffered human plasma was brought to 50% saturation with ammonium sulfate. The supernatant was fractionated on S-Sepharose (Pharmacia, Piscataway, N.J.). (Bed size: 5×12 cm or 1.5×10 cm) chromatography was performed in 20 mM NaAc, pH5.9. Proteins were eluted with a linear gradient of 0 to 0.2M NaCl at 5° C. Protein containing peak fractions were collected and pooled. Biologically active peak fractions were collected, pooled and loaded onto a Matrex-Gel P60 column equilibrated in 50 mM glycine - NaOH, pH9.0. Non-specifically bound material was eluted with 1M NaCl. A step gradient of sorbitol in equilibration buffer was applied to develop the glycosylated albumin shown in the SDS/PAGE on lanes 1, 2, 3 and 4, containing 3, 1.5, 0.75, and 0.375 µg protein, respectively (FIG. 3). Western blots (see description in Example 4) of active EGA fractions isolated by S-Sepharose sorbitol gradient chromatography were prepared and tested for with anti-albumin antiserum and wheat germ as well as s. nigra lectins (FIG. 6, lanes 1, 2 and 3 respectively).

Alternatively or additionally, glycoalbumin can be purified by boronate affinity chromatography as shown in Example 2.

EXAMPLE 2

Boronate Affinity Chromatography

Chromatography is usually performed at 5 C. using a 1.5×9 cm. column packed with P60 resin (Amicon, Danvers, Mass.) and equilibrated with 50 mM glycine/NaOH, pH 9.0. Samples to be fractionated are first dialyzed against a large excess of equilibration buffer and applied to the column at a flow of 1 ml/min. The column is developed using a step gradient of equilibration buffer containing varying concentrations of sorbitol. Prior to the application of the gradient, non-specifically adsorbed material is removed by washing the column with equilibration buffer containing 1M NaCl. A typical elution protocol would be elution with 5, 10, 20 50 and 100 mM sorbitol, followed by elution with 20 mM NaAc/0.6M NaCl, pH 4.0. Pools of eluted material are dialyzed against 20 mM Tris/150 mM NaCl, pH 7.5 and tested for biological activity as described in Examples 10 through 13.

EXAMPLE 3

Schiff Reaction of EGA

Figure 4:
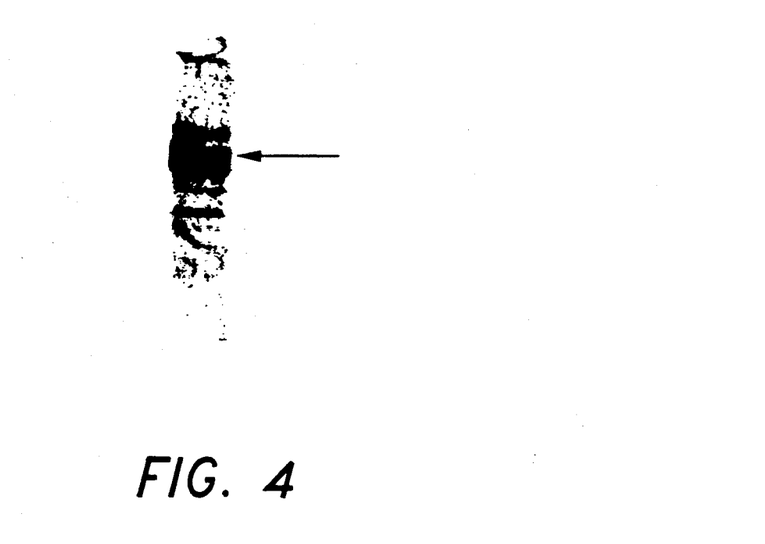
FIG. 4 A Schiff-stained SDS/PAGE (10% w/v polyacrylamide) of partially purified bovine albumin column fraction (3M NaCl eluate from S-Sepharose) indicating glycosylation; albumin bands are indicated by arrow.

In order to identify the glycosylated albumin band(s) in gels (PAGE SDS), the gels are fixed in 10% acetic acid/50% methanol and subsequently rinsed in water for 1 hour. Thereafter, the gels are treated with 0.5% (w/v) periodic acid for two hours at room (ambient) temperature, then rinsed briefly with water. After rinsing, gels are immersed in 0.5% w/v sodium arsenite in 5% (v/v) acetic acid for 30 min., then in 0.1% w/v sodium arsenite in 5% (v/v) acetic acid for 10 min. Treated gels are immersed in Schiff's Reagent (Sigma) overnight in the dark, followed by rinsing in excess amounts of 0.6% (w/v) sodium bisulfite in 0.01M HCL (FIG. 4).

Figure 9:
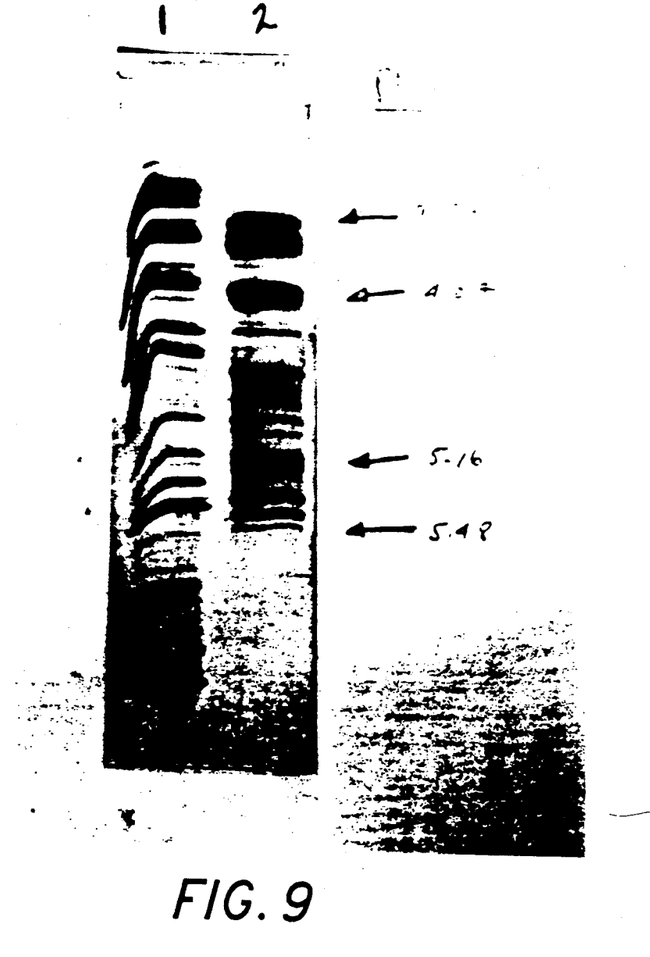
FIG. 9 Isoelectric focusing gel (pH 3–10) stained with C.B. for analysis of the observed pI's of the biologically active fraction (=EGA) isolated from human plasma by ammonium sulfate precipitation and molecular sieving column chromatography (Sephacryl S-300 HR; Pharmacia). Arrows indicate the observed pH at the various points along the gel lane (left: IEF markers; right: biologically active S 300 HR pool) of the agarose IEF gel (FMC Bioproducts).

With reference to FIG. 9, slab gel isoelectric focusing of EGA revealed several bands patterned in the range between PH 3.5 and 5.4, thereby indicating microheterogenesity within the isolated active fractions.

The glycosylated albumin fractions on polyacrylamide gels were analyzed for identity and glycosylation by means of the Western blot technique.

EXAMPLE 4

Western Blot Analysis of EGA Preparations

Figure 5:
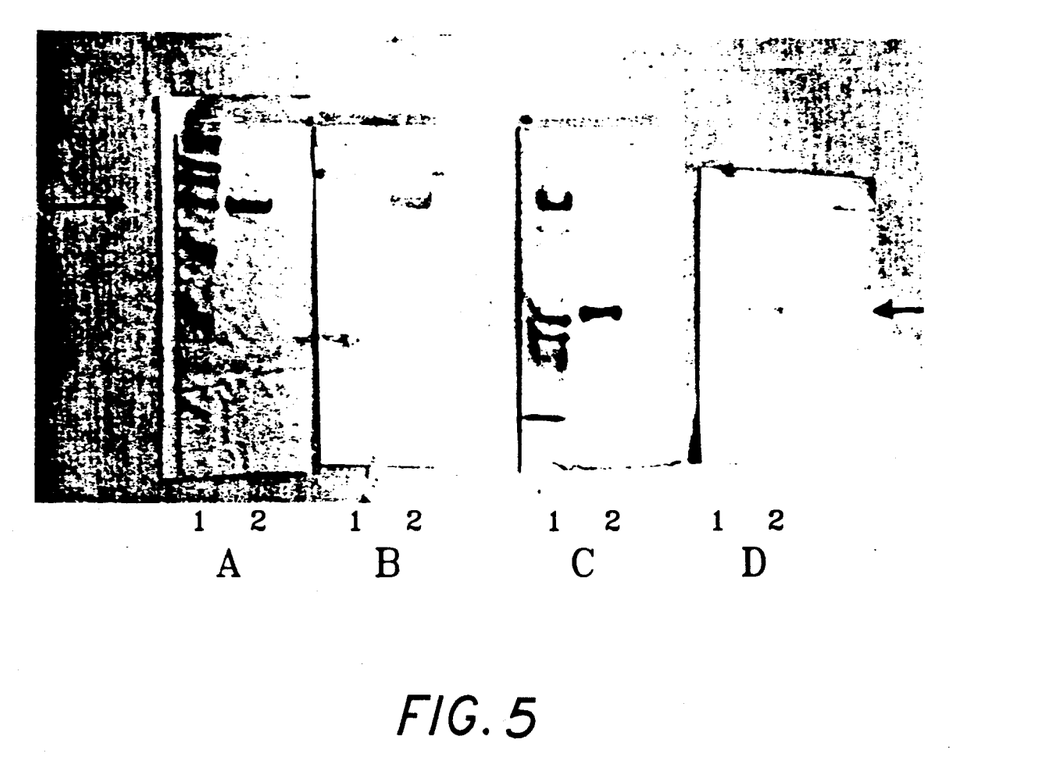
FIG. 5 Western blot analysis of 150 mM sorbitol eluate of human plasma boronate affinity chromatography on SDS/PAGE and nondenaturing PAGE
  A. Coomassie blue (C.B.) stained SDS/PAGE gel;
  B. Western blot with anti-human antibodies;
  C. Non-denaturing gel, C.B. stained;
  D. Western blot with anti-human antibodies; albumin position indicated by arrows.

Proteins were separated by polyacrylamide gel electrophoresis according to Laemmli (cited above) with or without SDS and blotted to nitrocellulose filter membranes (S&S, Keene, N.H.) in an LKB Ultrablot apparatus in accordance with manufacturer's instructions. The immunoblots were blocked with 5% w/v non-fat dry milk before exposure to anti-albumin antibodies. Lectin-probed blots were blocked using 5% w/v fraction V bovine serum albumin (BSA) Antibodies and lectins were incubated with the membranes for 1-2 hours at appropriate dilutions. Bound antibodies were detected with secondary, anti-rabbit antibodies and chromophores as supplied in a kit (Amersham, Chicago, Ill.) (FIG. 5). The lectins obtained from Sigma Chemical Co (St. Louis, Mo.) were biotinylated. After incubation and rinse the bound lectins were identified by WBT/BCIP chromatophores obtained in a kit from Zymed (San Francisco, Cal.).

Western blots of EGA purified from human plasma through the S-Sepharose and gel filtration chromatography steps described above showed strong reactions with wheat germ lectin (*Triticum vulgaris*), which is specific for N-acetyl-D-glucosamine and tri-N-acetyl-D-glucosamine. Similarly, EGA reacted with sialic acid-specific lectin (*Sambuca nigra*) (FIG. 6). It was found that EGA also adsorbed lectins derived from *Caragana arborescens*, specific for N-acetyl-D-galactosamine, and *Lycopersicon esculentum*, specific for tri-N-acetyl-D-galactosamine. The Western blot reaction with terminal mannose-specific lectin of *Galanthus rivalis* was barely detectable.

In order to determine the role of glycosylation in the growth promoting activity of purified glycosylated albumin fractions were treated with endoglycosidases and exoglycosidases and then subjected to the bioassay. The results further demonstrate the presence of oligosaccharide moieties on EGA.

EXAMPLE 5

Endoglycosidase Digestion (Table I)

The Q-Sepharose purified albumin fractions (EGA) were treated with endoglycosidases to remove the glycosylated moiety. Specifically, N-linked oligosaccharides were removed by incubation of the protein fractions with N-glycosidase F (Boehringer Mannheim, Indianapolis, Ind.) in 100 mM tris-HCL, pH7.0 for about 24 hours at 35° C. Protein concentration were approximately 1-4 mg/ml The reaction mixtures contained 1 ml protein solution, 1.25U enzyme, and 5 mM EDTA. Glycopeptidase F (Sigma) was used at a concentration of 2.5U with 1 ml protein solution in 100 mM sodium acetate, pH6.0 and incubated as above.

Neuraminidase treatment did not inhibit EGA activity, whereas digestions with endoglycosidase F plus N-glycosidase F were effective. Similarly, treatment of EGA with trypsin or chymotrypsin abolished growth promoting effect of EGA on CHO cells.

Removal of N-linked oligosaccharides was found to inhibit the growth promoting activity in CHO cells.

TABLE I

| Enzyme Sensitivity of Q-9 Fractions (Bovine) | |
|---|---|
| Treatment | Post-Treatment Growth of CHO Cells |
| Q-9 pH 5.1 control | + |
| Q-9 + neuraminidase | + |
| Cells + neuraminidase | + |
| Q-9 pH 7.0 control | + |
| Q-9 + endo F/glyco-F | − |
| Cells + endo F/glyco-F | + |
| Q-9 pH 8.0 control | + |
| Q-9 + trypsin | − |
| Q-9 + chymotrypsin | − |
| Cells + trypsin/chymotrypsin | + |
| EGA + O-glycanase | +/± |

Human EGA Activity Was Also Tested for Sensitivity to O-Glycanase

Moreover, O-linked oligosaccharides were removed by incubation of protein fractions with 12.5 mU 0-glycanase (Oxford Glycosystems, Rosedale, N.Y.) per milliliter of protein solution in 5 mM calcium chloride, thereby slightly diminishing bovine EGA activity. Neuraminidase (0.125 U/ml protein solution) was also included to remove any terminal sialic acid residues blocking 0-glycanase activity.

The degree of glycosylation and its effect on the cell growth promoting activity of glycosylated albumin was further explored by bioassay after digestion with exoglycosidases. The results are shown on Table I.

EXAMPLE 6

Exoglycosidase Sensitivity of CHO Cell Growth Promotion By Glycosylated Albumin Specifically, the exoglycosidase digestions of EGA fractions were assessed in 200 µl aliquots of fractions containing glycosylated albumin (1-2 mg/ml protein) incubated with the addition of the following enzymes: alpha glucosidase, 10 U, 100 mM NaAc, pH 6.8; beta glucosidase, 10 U, 100 mM NaAc, pH5.0; alpha galactosidase, 1U, 100 mM NaAc, pH 6.5; beta galactosidase 10 U, 100 mM Tris HCl pH 7.3; alpha mannosidase, 1U, 100 mM NaAc, pH5.0; beta mannosidase, 0.25 U, 100 mM NaAc, pH5.0; alpha fucosidase, 0.25 U, 100 mM NaAc, pH5.0. All the exoglycosidase reaction mixtures also contained 5 mM $CaCl_2$ and neuraminidase, 0.01 U (Boehringer Mannheim). Controls contained buffer instead of enzymes and were treated identically. Incubations were held for 24 hours at 35° C.

The results (Table II) show that neuraminidase treatment alone did not inhibit the growth promoting activity of EGA as tested by bioassay of CHO cells, in vitro. Similarly, alpha galactosidase did not interfere with the EGA growth effect on CHO cells (in vitro). Although the characterization is not yet final, results show that digestions in two experiments with beta glucosidase, alpha mannosidase and beta mannosidase inactivated EGA activity. However, the effect of digestions with alpha glucosidase, beta galactosidase, and alpha fucosidase is still inconclusive.

TABLE II

Exoglycosidase Sensitivity of CHO Cell Growth Promotion by Glycosylated Albumin

| ENZYME TREATMENT (a) | GROWTH OF CHO CELLS AFTER TREATMENT (b) |
|---|---|
| Alpha Glucosidase | +/− (c) |
| Beta Glucosidase | − |
| Alpha Mannosidase | − |
| Beta Mannosidase | − |
| Alpha Galactosidase | + |
| Beta Galactosidase | +/− (c) |
| Alpha Fucosidase | +/− (c) |
| Neuraminidase Alone | + |

(a): all samples were treated with the listed glycosidase and neuraminidase concurrently, except as indicated.
(b): two experiments
(c): +/−: variable effect or quantitative effect.
Different results observed in two experiments.

It has been discovered that the growth promoting or activating effect of EGA is relatively broad as it is not specific to a particular species. Moreover, a variety of cell cultures of different species origin have been tested and found to be receptive to growth stimulation by EGA (see Table III). Depending on the ambient conditions, developmental program or differentiation stage of the particular cells or cell lines, the instant EGA preparations may modulate growth by activating, retarding or inhibiting growth or even causing or aiding differentiation or quasi differentiation.

TABLE III

Growth Promoting Activity of Human Glycosylated Albumin With Various Cell Types

| CELL LINE | SPECIES | TISSUE | CELL TYPE | MEDIUM | SUPPLIER |
|---|---|---|---|---|---|
| CHO-K1 | HAMSTER | OVARY | FIBROBLAST | F12/MCDB302 | GIBCO |
| MDCK | DOG | KIDNEY | EPITHELIAL | MEM | GIBCO |
| MDBK | BOVINE | KIDNEY | EPITHELIAL | MEM | GIBCO |
| WI-38 | HUMAN | LUNG | FIBROBLAST | DMEM | GIBCO |
| VERO | MONKEY | KIDNEY | EPITHELIAL | M199 | GIBCO |
| *PRIMARY | HUMAN | UMBILICAL VEIN | ENDOTHELIAL | RSM210 | VEC TEC |

*with use of Matrigel as extracellular matrix.

As shown in Table III, cell lines derived from various kinds of tissue that have been tested so far are stimulated to grow in the presence of the instant enzymatically glycosylated albumin (EGA). At concentrations as low as 10 μg/ml culture media cell adherence and replication has been observed. Therefore, cells thriving on EGA supplemented media include the epithelial, endothelial, and fibroblast varieties.

EXAMPLE 7

Cell Surface Localization of Glycoalbumin

Monolayers of Chinese hamster ovary (CHO-K1) cells were cultured for 3 days in basal media (Ham's F12; GIBCO) containing approximately 100 μg/ml bovine or human glycosylated albumin fractions isolated by S-Sepharose chromatography. After removing the media from the tissue culture flasks, the monolayers were exposed to 1 mM disuccinimidyl suberate (Pierce, Rockford, Ill.) for 40 min. at 0° C. Subsequently, the monolayers were rinsed four times in cold phosphate buffered saline. Cells were then incubated with anti-albumin antibodies directed against bovine or human albumin (USB, Cleveland, Ohio or Cappel, Durham, N.C.). Cell-bound antibodies were detected with an Amersham biotin-streptavidin secondary antibody detection kit using NBT/BCIP chromophores. Controls included cultures which were identically treated identically while omitting the antibodies to albumin or using preimmune IgG fractions.

In the absence of either FBS or EGA supplement the cells fail to adhere and die.

EXAMPLE 8

Flow Cytometry

The apparent cell state specificity of EGA receptors was determined by a flow cytometric method. In one particular experiment, CHO cells were grown in the presence of S-Sepharose-purified glycosylated albumin fractions from bovine plasma wherein the albumin moiety was conjugated with FITC isoform 1 (Sigma), according to standard procedure. As described above, the cell monolayers were treated with disuccinimidyl suberate and released from the surface of culture flasks by means of enzyme-free disassociation buffer (GIBCO).

The isolated cells were fixed with 0.5% paraformaldehyde at 5° C., treated with 0.1% (v/v) Triton X-100 in PBS (phosphate buffered saline) for 5 min. at 5° C. and washed with PBS. DNA was stained with propidium iodide (concentration of 50 μg/ml) after treatment with RNase (Sigma, 300 U/ml PBS) for 30 min. at 37° C.

Cells were analyzed with a Coulter Epics flow cytometry instrument In the figure, the X axis is proportionate to DNA fluorescence, the Y axis is proportionate to FITC-albumin (FITC-EGA) fluorescence. The arrow indicates the location of DNA fluorescence of cells being located covering mostly in the $G_0/G_1/S$ portion of the cell cycle. Indeed, the majority of albumin fluorescent cells (Y-axis) is found on this part of the X-axis. In sum, the data support the conclusion that the receptors (binding EGA) are predominantly expressed at $G_0/G_1/S$ boundary (FIG. 1).

Taking now reference to FIG. 9 the following Example demonstrates the binding of EGA with human blood cells as measured by flow cytometry.

EXAMPLE 9

Interaction of Human Buffy Coat Cells With Glycosylated Albumin

Preparation of Glycosylated Albumin (EGA). EGA was purified by S-Sepharose and molecular sieve chromatography as described. The protein content was adjusted to approximately 2 mg/ml. The sample was dialyzed against an excess of 50 mM glycine-NaOH, pH 9.0 buffer at 5° C., FITC (isomer 1-Sigma) was dissolved in DMSO at a concentration of 1 mg/ml. FITC was slowly and very gradually added in equal amounts to dialyzed EGA up to a concentration of 50 µl FITC solution/ml EGA with constant agitation at 5° C. The solution was slowly stirred overnight at 5° C. after addition of FITC was completed. Unbound fluorochrome was removed by molecular sieve chromatography (Sephacryl S300HR-Pharmacia in 20 mM Tris-150 mM NaCl, pH 7.5 at 5C., TBS).

FITC-labelled EGA (protein: 13 mg/ml) was diluted 10 fold in Dulbecco's phosphate buffered saline Buffy coat cells from human peripheral blood were prepared from EDTA anticoagulated blood by low speed centrifugation and washed several times with RPMI 1640 (GIBCO). The cell pellet containing several million cells is resuspended in 1 ml of FITC-EGA and incubated 60 min. at 0° C. Freshly prepared DSS is added to cells as described for cell surface detection of albumin binding to CHO cells (as described above) and incubated at 0° C. for 60 min. Cells are then washed with PBS, resuspended in 0.5% paraformaldehyde dissolved in saline and stored at 5° C., until analysis on an Epics Profile Analyzer (Coulter Electronics). As a control, buffy coat cells are treated with Tris-buffed saline instead of FITC-EGA.

Figure 8A:
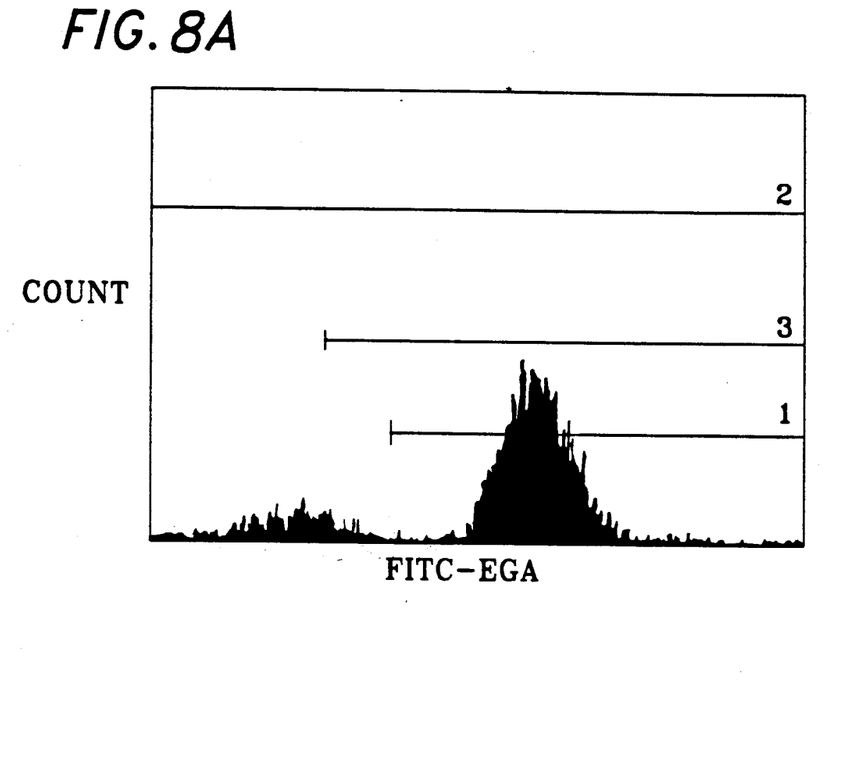
FIG. 8 Cytoflow analysis of interaction of human buffy coat derived cells and FITC labelled EGA.
Figure 8B:
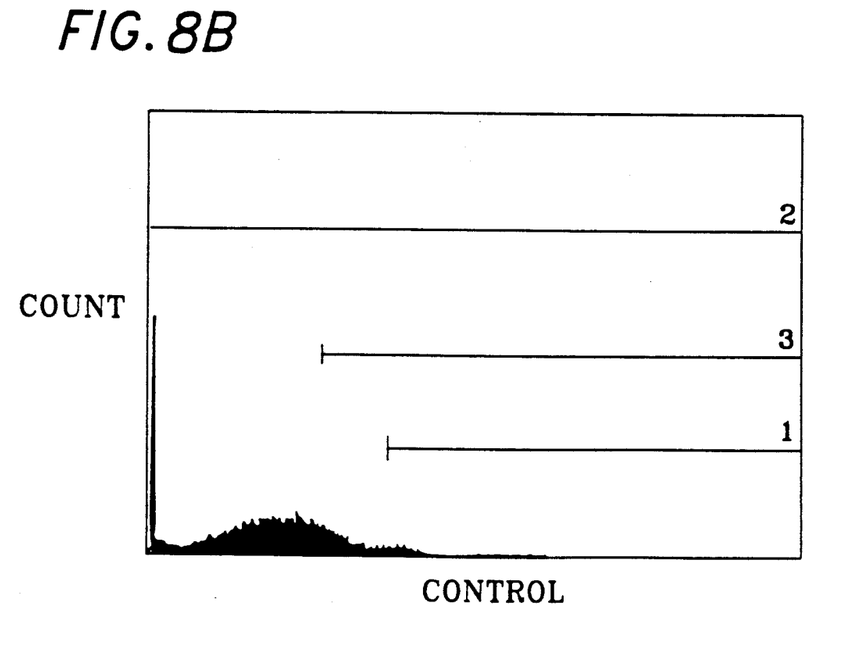

In one experiment, 73,000 Control and 106,000 FITC-EGA treated cells were analyzed for fluorescence and for light scattering characteristics. The data obtained is illustrated in FIG. 8. No significant fluorescence of erythrocytes was noted when the cells were subjected to this procedure (data not shown).

The results shown in FIG. 8 clearly indicate a fluorescent cell population which is absent in the autofluorescence control. The FITC-EGA tagged cells were gated by light scattering and designated as a distinct population.

EXAMPLE 10

Glycated Human Albumin Effect

Moreover, no growth was observed in CHO cell cultures incubated in the presence of nonenzymatically glucose-substituted human albumin (glycated albumin, Sigma) at minimum concentrations of 200 µg/ml using human albumin glycated with 1-4 hexose/mole of albumin.

The growth-supporting effect of EGA appears to be substantially similar to that of whole serum, e.g. fetal bovine serum, as demonstrated in the following experiments (Example 11). However, the results show that there may be some differences, too.

EXAMPLE 11

Morphological Effect on CHO Mutants

Further observations on the effect of glycosylated albumin were made on CHO mutants expressing altered amounts of cell surface proteoglycans Cells lacking cell surface heparin sulfate or chondroitin sulfate exhibited similar morphological appearance in cultures whether grown in glycosylated albumin or FBS.

However, cells of a CHO mutant cell line 677, which overexpresses chondroitin sulfate about 3-fold over the normal strain, exhibit an ovoid appearance in glycosylated albumin (EGA) containing media, in contrast to their mostly fibroblast-like morphology in FBS supplemented media. Cells grown in glycosylated albumin fortified media were determined to bind the albumin as, e.g., by the immunocytochemical procedure, as described above.

EXAMPLE 12

Figure 7A:
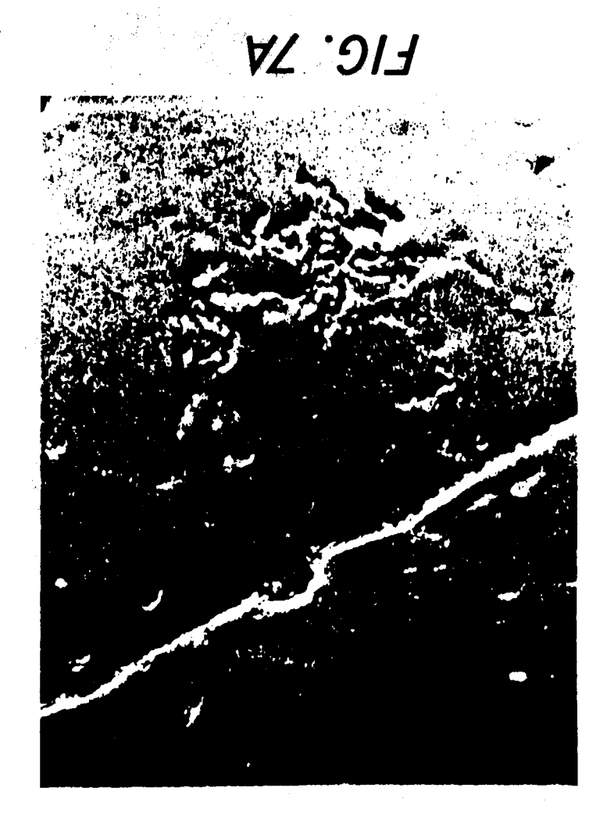
Figure 7B:
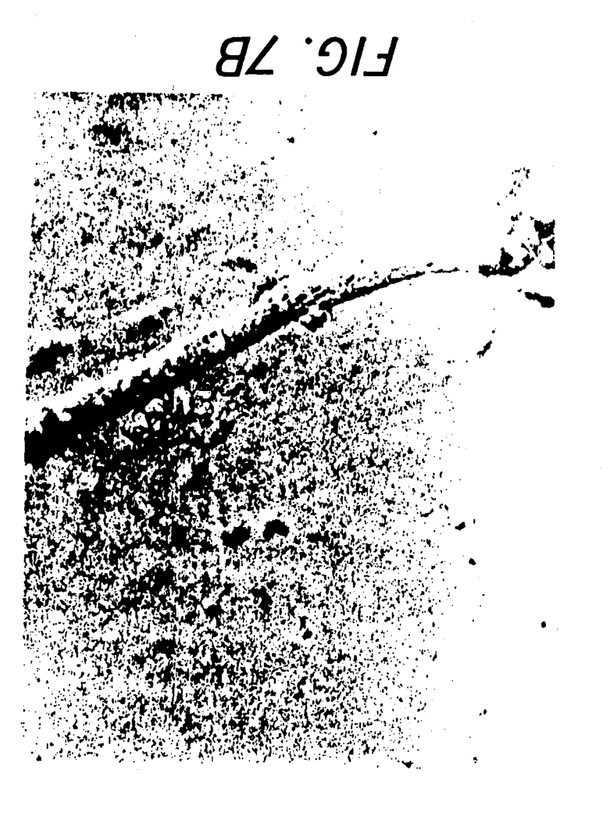

Human Umbilical Cord Endothelial Cells (h-UCE) (FIG. 7)

In addition to the above-recited observations on CHO cells, glycosylated albumin fractions were used to assess the EGA effect on human umbilical cord endothelial cells when cultured on a differentiation system comprising RSM 210 (VecTec, Schenectady, N.Y.) and Matrigel (Collaborative Biomedical Products, Medford, Mass.), a gelling growth matrix. Control incubations contained matrigel and medium 199, RSM 210 or 10% FBS. These human primary cell isolates were previously reported to form processes resembling capillaries (Madri, et al. *J. Cell Biol.* 106, 1988, 1375–1384.

While h-UCE cultures in the presence of matrigel with partially purified albumin (EGA) preparations showed capillary-like processes, cultures on Matrigel alone did not (see FIG. 3). EGA may therefore effect differentiation events as well as growth of primary, nontransformed cell lines.

Further, the growth effect studies appear to indicate that the glycoalbumin additive (EGA) promotes in serum-free primary cell cultures e.g growth and differentiation of cultured monocytes to macrophages within days.

EXAMPLE 13

Human Monocyte-Macrophage Differentiation

Human peripheral blood was taken by venipuncture, citrated to prevent coagulation and centrifuged at low speed. The buffy coat is removed by aspiration and diluted twofold with phosphate buffered saline solution (PBS). It is then layered onto Ficoll-Paque (Pharmacia) at a ratio 2 vols: vol Ficoll-Paque. The mixture is centrifuged at 1200xg for 45 minutes at room temperature. The cellular contents are concentrated in a discrete band at the Ficoll-Paque/buffer interface. The cells are removed by aspiration and sedimented by low speed centrifugation, washed 2 times with RPMI 1640 (GIBCO) and diluted with this medium containing autologous human serum at 10% (v/v) concentration. The cells are then subjected to a simple selection regimen by placing them into standard plastic tissue culture ware at an approximate density of $2 \times 10^6$ cells/ml. After incubation of one hour at 37° C. in 5% $CO_2$ in air, non-adherent cells and blood elements are removed by rinsing the plated cells with warm RPM1 1640 without serum two times. The remaining cells are incubated in medium containing autologous serum. After about 24 hours in culture, the cells are again rinsed with warm (37° C.) serum-free medium and reincubated with serum supplemented medium. In testing the various factions isolated from serum or plasma, the different quantities are substituted for serum in the suitable media, after several rinses of the cells with serum-free medium. Alternatively, the various fractions or purified factors may be tested by directly adding them to the cultures which have previously been rinsed with warm basal medium.

It has further been determined that, similar to albumin, the liver is also the major if perhaps not the only source for glycosylated albumin (EGA). This conclusion is supported by the discovery that glycosylated albumin is also expressed in hepatoma cells. In particular, HEP G2 cell cultures showed enriched presence of human glycosylated albumin, EGA, in conditioned media, as described below.

The HEP G2 cell line is commercially available from the American Type Culture Collection, Deposit No. HB 8065, and from the Wistar Institute, Philadelphia, Pa.

EXAMPLE 14

Albumin Expression By Hepatoma Cells

Conditioned media of cultured HEP G2 cells (human hepatoma - derived cell line) were fractionated by SDS-PAGE and western blots thereof subjected to incubation with antibodies to human albumin. The western blots were found albumin-positive. Based on standard comparison, there was an estimated concentration of 20–30 $\mu$g albumin/ml medium. Coomassie blue staining of the protein disclosed one major protein band migrating similary to human albumin molecular weight standard (66,200 d.).

Other western blots of the hepatoma - conditioned media using lectin probes demonstrated reactivity of blot-identified albumin bands suggesting the presence of sialic acid and N-acetylglucosamine in the albumin containing blots. Moreover, the glycosylation of the instant albumin is an intracellular event and not a consequence of peripheral circulation or, more particularly, by modifying serum enzymes.

The purification of hepatoma culture - derived glycosylated albumin fractions points the way to the utility of such a cell line as HEP G2 to also produce a human glycosylated albumin growth factor by recombinant DNA technology. For instance, gene amplification can provide substantially increased in vitro production of EGA.

A preferred embodiment of the present invention relates to compositions containing glycosylated albumin (EGA) that enhance growth and productivity of cells and tissues in culture media, at concentrations of EGA varying from 1–300 $\mu$g/ml medium.

Similarly, compositions of EGA may have efficacious use in the treatment of wounds for their potential wound healing effect. Particularly in view of the known presence of albumin in edemas or wounds, it is suggested that the newly identified EGA may play a biological role in wound repair.

Potentially useful embodiment of the present invention provides a diagnostic test of liver function and pathology thereof, which test can include an assay of circulating glycosylated albumin (EGA) fractions and ratio or percentage of EGA to total or unglycosylated albumin or pathological change thereof. The diagnosis may depend on procedures utilizing serological or chromatographic measurements including isolation, purification, and biological activity assays. The lectin adsorbancy test described above also serves to separate EGA from other, nonenzymatically "glycated" albumins.

Another potentially useful embodiment comprises the use of EGA assay for detecting liver cancer. The assay can utilize a combination of serological and chemical methods, as e.g., immunoassay and lectin binding of circulating EGA.

The present invention also provides a pharmaceutical composition, which comprises an EGA fraction from a suitably homologous species and a pharmaceutically acceptable carrier for topical use.

The dose of the EGA fraction used in the treatment of wounds, especially on the skin, will vary with the relative efficacy of the EGA material. However, as a general guide, applicable concentrations may range from about 1 $\mu$g/ml to about 500 $\mu$g/ml. Such amounts may be administered more than once a day, for example, several times a day, continuing over several days or weeks as long as such a treatment is needed.

Within the preferred range indicated above, the EGA preparation is not expected to have toxic effects. The preferred embodiment of the topical treatment of wounds is intended as utilizing EGA fraction derived from human serum or plasma for treatment of human skin. Similarly, in the case of other warmblooded animals, the EGA fractions of the invention are isolated from the identical species which is to be treated in order to avoid possible rejection or other immuno-toxic effects.

For topical and percutaneous administration, the preparations may also be presented as an ointment, cream, lotion, gel, spray, aerosol, wash, skin paint or patch.

A composition of an effective amount of EGA fractions for topical or percutaneous use may also contain antioxidants, vitamins, amino acids, carbohydrates, lipids, trace metals, minerals, physiologically amenable salt solutions or buffers, as well as antibiotics and tissue activity modifying agents as tissue plasminogen activators or other factors.

While the present invention has been described above with reference to the preferred embodiments thereof, it should be apparent to those skilled in the art that various modifications and changes in the process can be incorporated without departing from the true spirit of the invention as defined in appended claims.

What is claimed is:

1. A growth factor comprising enzymatically glycosylated albumin of the type occurring in the hepatoma cell line HEP G2 wherein said growth factor is substantially purified and is active in promoting the growth of mammalian cells in vitro.

2. An enzymatically glycosylated albumin in isolated or purified form comprising at least one oligosaccharide moiety linked to an albumin and further comprising mammalian cell growth promoting and/or modulating activity.

3. The glycosylated albumin according to claim 2, derived from bodily fluids.

4. The glycosylated albumin according to claim 3, wherein the bodily fluids are mammalian.

5. The glycosylated albumin according to claim 4, wherein the mammalian bodily fluids are human.

6. The glycosylated albumin according to claim 2, derived from cell, tissue or organ culture, in vitro.

7. The glycosylated albumin according to claim 6, wherein the culture comprises hepatoma cells.

8. The glycosylated albumin according to claim 2, wherein the growth promoting and/or modulating activity comprises said albumin binding to cells.

9. The glycosylated albumin according to claim 8, wherein binding is related to a particular growth phase.

10. The glycosylated albumin according to claim 2, wherein the oligosaccharide moiety comprises sialic acid or N-acetylglucosamine moieties.

11. The glycosylated albumin according to claim 2, comprising lectin-binding activity.

12. The glycosylated albumin according to claim 11, wherein the lectin binding activity comprises wheat germ lectin (*T. vulgaris*) or elderbark lectin *Sambucus nigra*.

13. The glycosylated albumin according to claim 5, wherein the human bodily fluid-derived glycosylated albumin comprises an N-terminal amino acid sequence identical with human serum albumin.

14. The glycosylated albumin according to claim 2 comprising serological similarity with albumin.

15. The growth factor of claim 1 wherein the glycosylated albumin comprises:
    (a) an apparent M.W. of at least 65,000 daltons on SDS/PAGE;
    (b) serologically identified albumin;
    (c) binding to N-acetyl-D-glucosamine or sialic acid specific lectins;
    (d) deglycosylated and/or desialylated by specific glycosidases;
    (e) binding to a cell surface receptor; and
    (f) activating and/or modulating cell growth.

16. A composition for cell, tissue or organ culture media comprising the growth factor according to claim 15.

17. The composition for cell, tissue or organ culture media according to claim 16 which are serum-free.

18. A glycoprotein isolated from mammalian sources comprising an apparent molecular weight of at least 65,000 daltons on SDS/PAGE, identified serologically and enzymatically as a glycosylated form of albumin having growth promoting activity.

19. The glycoprotein according to claim 18 comprising a product of a hepatoma cell culture.

20. The glycoprotein according to claim 19 wherein the product is isolated from conditioned media of the hepatoma cell culture.

21. A pharmaceutical composition comprising the glycosylated albumin of claim 1 and a pharmaceutically acceptable carrier.

22. A method of topical or percutaneous treatment of tissue that is in need of growth factor treatment in a warmblooded animal, which comprises administering to the animal an effective amount of the glycosylated albumin according to claim 1 with a pharmaceutically acceptable carrier in a manner designed to deliver said glycosylated albumin to the tissue in need of treatment.

23. A process for purifying the glycosylated albumin of claim 1 which comprises salt precipitation; ion exchange chromatography; gel filtration; molecular sieve filtration or dialysis; lectin affinity chromatography; gel electrophoresis; and a bioassay for selecting fractions of the glycosylated albumin with growth promoting activity.

* * * * *